(12) United States Patent
Carson et al.

(10) Patent No.: US 7,671,018 B2
(45) Date of Patent: Mar. 2, 2010

(54) DELIVERY SYSTEM FOR HEPARIN-BINDING GROWTH FACTORS

(75) Inventors: Daniel D. Carson, Hockessin, DE (US); Mary C. Farach-Carson, Hockessin, DE (US); Margaret French, Houston, TX (US); Ronald Gomes, San Jose, CA (US); Rupert Timpl, Gaüting (AT)

(73) Assignee: University of Delaware, Newark, DE (US)

( * ) Notice: Subject to any disclaimer, the term of this patent is extended or adjusted under 35 U.S.C. 154(b) by 0 days.

(21) Appl. No.: 10/363,368

(22) PCT Filed: Aug. 27, 2001

(86) PCT No.: PCT/US01/26512

§ 371 (c)(1), (2), (4) Date: Aug. 4, 2003

(87) PCT Pub. No.: WO02/17955

PCT Pub. Date: Mar. 7, 2002

(65) Prior Publication Data

US 2004/0063619 A1    Apr. 1, 2004

Related U.S. Application Data

(60) Provisional application No. 60/228,935, filed on Aug. 30, 2000.

(51) Int. Cl.
*A61K 38/17* (2006.01)
*A61K 38/18* (2006.01)
*A61L 27/40* (2006.01)
*C07K 14/47* (2006.01)
*C07K 14/475* (2006.01)

(52) U.S. Cl. .................. 514/12; 530/350; 530/395; 424/422

(58) Field of Classification Search .............. 514/8; 530/395, 399; 424/423, 484
See application file for complete search history.

(56) References Cited

U.S. PATENT DOCUMENTS 5,206,023 A * 4/1993 Hunziker .............. 424/423
5,661,127 A * 8/1997 Bhatnagar et al. ........ 514/16
5,842,477 A * 12/1998 Naughton et al. ........ 128/898
6,514,514 B1 * 2/2003 Atkinson et al. ........ 424/423

FOREIGN PATENT DOCUMENTS

WO   WO 98/08381 A1    3/1998
WO   WO 99/06054 A1    2/1999

OTHER PUBLICATIONS

Aviezer et al. Perlecan, basal lamina proteoglycan, promotes basic fibroblast growth factor-receptor binding, mitogenesis, and angiogenesis. Cell. Dec. 16, 1994;79(6):1005-13.*

Kawaguchi et al. Stimulation of fracture repair by recombinant human basic fibroblast growth factor in normal and streptozotocin-diabetic rats. Endocrinology. Aug. 1994;135(2):774-81.*
Sasaki et al. Inhibition of glycosaminoglycan modification of perlecan domain I by site-directed mutagenesis changes protease sensitivity and laminin-1 binding activity. FEBS Lett. Sep. 18, 1998;435(2-3):169-72.*
Rescan et al. Distribution and origin of the basement membrane component perlecan in rat liver and primary hepatocyte culture. Am J Pathol. Jan. 1993;142(1):199-208.*
Whitelock et al. The degradation of human endothelial cell-derived perlecan and release of bound basic fibroblast growth factor by stromelysin, collagenase, plasmin, and heparanases. J Biol Chem. Apr. 26, 1996;271(17):10079-86.*
Ko et al. Cyclic AMP regulates basement membrane heparan sulfate proteoglycan, perlecan, metabolism in rat glomerular epithelial cells. Mol Cell Biochem. Sep. 6, 1996;162(1):65-73.*
Cuevas et al. Basic fibroblast growth factor (FGF) promotes cartilage repair in vivo. Biochem Biophys Res Commun. Oct. 31, 1988;156(2):611-8.*
Nakajima Characterization of the cells in the repair tissue of full-thickness articular cartilage defects. Histochem Cell Biol. Apr. 1998;109(4):331-8.*
Iozzo et al. The biology of perlecan: the multifaceted heparan sulphate proteoglycan of basement membranes and pericellular matrices. Biochem J. Sep. 15, 1994;302 ( Pt 3):625-39.*
Atkinson et al. Combination of osteoinductive bone proteins differentiates mesenchymal C3H/10T1/2 cells specifically to the cartilage lineage. J Cell Biochem. Jun. 1, 1997;65(3):325-39.*
Costell et al. Perlecan maintains the integrity of cartilage and some basement membranes. J. Cell. Biol. Nov. 29, 1999, vol. 147, No. 5, pp. 1109-1122.
French et al. Expression of the heparan sulfate proteoglycan, perlecan, during mouse embryogenesis and perlecan chondrogenic activity in vitro. J. Cell. Biol. May 31, 1999, vol. 145, No. 5, pp. 1103-1115.
Graham et al. Expression of human perlecan domain I as a recombinant heparan sulfate proteoglycan with 20-kDa glycosaminoglycan chains. Biochemical and Biophysical Research Communications. Mar. 24, 1999, vol. 256, No. 3, pp. 542-548.
Costell et al. Characterization of recombinant perlecan domain I and its substitution by glycosaminoglycans and oligosaccharides. Eur. J. Biochem. Jan. 15, 1997, vol. 243, Nos. 1-2, pp. 115-121.
Groffen et al. Expression and characterization of human perlecan domains I and II synthesized by baculovirus-infected insect cells. European Journal of Biochemistry. Nov. 1, 1996, vol. 241, No. 3, pp. 827-834.
Sundarraj et al. Perlecan is a component of cartilage matrix and promotes chondrocyte attachment. J. Cell. Sci. Jul. 1995, vol. 108, Pt. 7, pp. 2663-2672.

(Continued)

*Primary Examiner*—David S Romeo
(74) *Attorney, Agent, or Firm*—RatnerPrestia (57) ABSTRACT

New uses of proteoglycans to bind and present growth factors, methods of accelerating wound, tissue or bone repair using such proteoglycans, pharmaceutical compositions of such proteoglycans, and scaffolds coated with such proteoglycans are disclosed. The proteoglycan of the invention is derived from domain I or perlecan.

10 Claims, 5 Drawing Sheets
(3 of 5 Drawing Sheet(s) Filed in Color)

OTHER PUBLICATIONS

Kokenyesi et al. Formation of heparan sulfate or chondroitin/dermatan sulfate on recombinant domain I of mouse perlecan expressed in Chinese hamster ovary cells. Biochemical and Biophysical Research Communications. Jun. 6, 1995, vol. 211, No. 1. pp. 262-267.

Reddi, A. Hari, "Cartilage Morphogenesis: Role of bone and Cartilage Morphogenetic Proteins, Homeobox Genes and Extracellular Matrix," Matrix Biology; 1994; vol. 14; pp. 599-606.

Lanske, Beate et al., "Ablation of the PTHrP gene or the PTH/PTHrP receptor gene leads to distinct abnormalities in bone development," The Journal of Clinical Investigation; Aug. 1999; vol. 104, No. 4; pp. 399-407.

Iwamoto, M. et al, "Actions of Hedgehog Proteins on Skeletal Cells," Crit. Rev. Oral Biol. Med.; 1999; vol. 10, No. 4; pp. 477-486.

Chintala, Shravan K. et al., "Basic Fibroblast Growth Factor Binds to Heparan Sulfate in the Extracellular Matrix of Rat Growth Plate Chondrocytes," Archives of Biochemistry and Biophysics; Apr. 1994; vol. 310, No. 1; pp. 180-186.

Ornitz, David M., "FGFs, heparan sulfate and FGFRs: complex interactions essential for development," BioEssays; 2000; vol. 22; pp. 108-112.

Arikawa-Hirasawa, Eri et al., "Perlecan is essential for cartilage and cephalic development," Nature Genetics; Nov. 1999; vol. 23; pp. 354-358.

Murdoch, Alan D. et al., "Primary Structure of the Human Heparan Sulfate Proteoglycan from Basement Membrane (HSPG2/Perlecan)," The Journal of Biological Chemistry; Apr. 25, 1992; vol. 267, No. 12; pp. 8544-8557.

Cohen, Isabelle R. et al., "Structural characterization of the complete human perlecan gene and its promoter," Proc. Natl. Acad. Sci. USA; Nov. 1993; vol. 90; pp. 10404-10408.

Costell, Mercedes et al., "Structual characterization of recombinant domain II of the basement membrane proteoglycan perlecan," FEBS Letters; 1996; vol. 396; pp. 127-131.

Schulze, Bettina et al., "Structural and Cell-Adhesive Properties of Three Recombinant Fragments Derived from Perlecan Domain III," Matrix Biology; 1996; vol. 15; pp. 349-357.

Brown, Judith C. et al., "The C-terminal domain V of perlecan promotes β1 integrin-mediated cell adhesion, binds heparin, nidogen and fibulin-2 and can be modified by glycosaminoglycans," Eur. J. Biochem.; 1997; vol. 250; pp. 39-46.

Costell, Mercedes et al., "Characterization of recombinant perlecan domain I and its substitution by glycosaminoglycans and oligosaccharides," Eur. J. Biochem.; 1997; vol. 243; pp. 115-121.

Sasaki, Takako et al., "Structure, function and tissue forms of the C-terminal globular domain of collagen XVIII containing the angiogenesis inhibitor endostatin," The EMBO Journal; 1998; vol. 17, No. 15; pp. 4249-4256.

Mongiat, Maurizio et al., "The Protein Core of the Proteoglycan Perlecan Binds specifically to Fibroblast Growth Factor-7," The Journal of Biological Chemistry; Mar. 10, 2000; vol. 275, No. 10; pp. 7095-7100.

San Antonio, James D. et al.; "Regulation of Chondrogenesis by Heparan Sulfate and Structurally Related Glycosaminoglycans," Developmental Biology; 1987; vol. 123; pp. 17-24.

Tavella, Sara et al., "N-CAM and N-Cadherin Expressions during In Vitro Chondrogenesis," Experimental Cell Research; 1994; vol. 215; pp. 354-362.

Perrimon, Norbert and Bernfield, Merton, "Specificities of heparan sulphate proteoglycans in developmental processes," Nature; Apr. 13, 2000; vol. 404; pp. 725-728.

Solursh, Michael, "Formation of Cartilage Tissue In Vitro," Journal of Cellular Biochemistry; 1991; vol. 45; pp. 258-260.

Walz, Andreas et al., "Essential role of heparan sulfates in axon navigation and targeting in the developing visual system," Development; 1997; vol. 124; pp. 2421-2430.

Sweigart, Mark A. and Athanasiou, Kyriacos A., "Toward Tissue Engineering of the Knee Meniscus," Tissue Engineering; 2001; vol. 7, No. 2; pp. 111-129.

Noonan, Douglas M. et al., "The Complete Sequence of Perlecan, a Basement Membrane Heparan Sulfate Proteoglycan, Reveals Extensive Similarity with Laminin A. Chain, Low Density Lipoprotein-Receptor, and the Neural Cell Adhesion Molecule," The Journal of Biological Chemistry; Dec. 5, 1991; vol. 266, No. 34; pp. 22939-22947.

* cited by examiner

SEQUENCE LISTING

```
<160> NUMBER OF SEQ ID NOS: 2

<210> SEQ ID NO 1
<211> LENGTH: 172
<212> TYPE: PRT
<213> ORGANISM: Human

<400> SEQUENCE: 1

Val Thr His Gly Leu Arg Ala Tyr Asp Gly Leu Ser Leu Pro Glu Asp
1               5                   10                  15

Ile Glu Thr Val Thr Ala Ser Gln Met Arg Trp Thr His Ser Tyr Leu
            20                  25                  30

Ser Asp Asp Glu Tyr Met Leu Ala Asp Ser Ile Ser Gly Asp Asp Leu
        35                  40                  45

Gly Ser Gly Asp Leu Gly Ser Gly Asp Phe Gln Met Val Tyr Phe Arg
    50                  55                  60

Ala Leu Val Asn Phe Thr Arg Ser Ile Glu Tyr Ser Pro Gln Leu Glu
65                  70                  75                  80

Asp Ala Gly Ser Arg Glu Phe Arg Glu Val Ser Glu Ala Val Val Asp
                85                  90                  95

Thr Leu Glu Ser Glu Tyr Leu Lys Ile Pro Gly Asp Gln Val Val Ser
            100                 105                 110

Val Val Phe Ile Lys Glu Leu Asp Gly Trp Val Phe Val Glu Leu Asp
        115                 120                 125
```

-continued

```
Val Gly Ser Glu Gly Asn Ala Asp Gly Ala Gln Ile Gln Glu Met Leu
        130                 135                 140

Leu Arg Val Ile Ser Ser Gly Ser Val Ala Ser Tyr Val Thr Ser Pro
145                 150                 155                 160

Gln Gly Phe Gln Phe Arg Arg Leu Gly Thr Val Pro
                165                 170

<210> SEQ ID NO 2
<211> LENGTH: 173
<212> TYPE: PRT
<213> ORGANISM: Mouse

<400> SEQUENCE: 2

Val Thr His Gly Leu Arg Ala Tyr Asp Gly Leu Ser Leu Pro Glu Asp
1               5                   10                  15

Thr Glu Thr Val Thr Ala Ser Arg Tyr Gly Trp Thr Tyr Ser Tyr Leu
                20                  25                  30

Ser Asp Asp Glu Asp Leu Leu Ala Asp Ala Ser Gly Asp Gly Leu
            35                  40                  45

Gly Ser Gly Asp Val Gly Ser Gly Asp Phe Gln Met Val Tyr Phe Arg
        50                  55                  60

Ala Leu Val Asn Phe Thr Arg Ser Ile Glu Tyr Ser Pro Gln Leu Glu
65                  70                  75                  80

Asp Ala Ser Ala Lys Glu Phe Arg Glu Val Ser Glu Ala Val Val Glu
                85                  90                  95

Lys Leu Glu Pro Glu Tyr Arg Lys Ile Pro Gly Asp Gln Ile Val Ser
                100                 105                 110

Val Val Phe Ile Lys Glu Leu Asp Gly Trp Val Phe Val Glu Leu Asp
            115                 120                 125

Val Gly Ser Glu Gly Asn Ala Asp Gly Ser Gln Ile Gln Glu Val Leu
        130                 135                 140

His Thr Val Val Ser Ser Gly Ser Ile Gly Pro Tyr Val Thr Ser Pro
145                 150                 155                 160

Trp Gly Phe Lys Phe Arg Arg Leu Gly Thr Val Pro Gln
                165                 170
```

DELIVERY SYSTEM FOR HEPARIN-BINDING GROWTH FACTORS

RELATED APPLICATIONS

This application is a national stage application (under 35 U.S.C. 371) of PCT/US01/26512 filed Aug. 27, 2001, which claims the benefit of U.S. Application No. 60/228,935 filed Aug. 30, 2000, which is hereby incorporated herein in its entirety.

GOVERNMENT INTERESTS

This invention was made with Government support under Grant (or Contract) No. HD25235 awarded by the National Institutes of Health. The Government has certain rights in this invention.

BACKGROUND OF THE INVENTION

The invention provides new uses and compositions of proteoglycans. The proteoglycans are derived from perlecan, an extracellular matrix protein. The inventive proteoglycans retain certain desirable activities of the full-length perlecan molecule, such as the ability to bind growth factors, yet they have a size that allows for effective preparation and application as is not the case for perlecan. Furthermore, large amounts of the inventive proteoglycan can be produced in mammalian cell lines. The inventive proteoglycans can be used as adhesive coatings on scaffolds used for bone and tissue repair to attract and retain growth factors to the repair site. The inventive proteoglycans can also be used to induce differentiation to or maintenance of chondrocyte phenotype.

Chondrogenesis occurs as a multi-step process that is initiated by condensation of mesenchymal stem cells that subsequently undergo a specific program of differentiation. Studies from several laboratories clearly have demonstrated a role for specific soluble signals in this differentiation program that include bone morphogenetic proteins (1), parathyroid hormone related protein (PTIrP)(2), Indian hedgehog (Ihh) (3), and transforming and fibroblast growth factors (4,5). Of interest, several of these are known to interact with heparan sulfate proteoglycans (HSPG), a factor implicated in modulating their bioavailability (6). It has been demonstrated that a large HSPG found in the extracellular matrix (ECM) of developing cartilage, perlecan (Pln, HSPG2), stimulated cells of a murine fibroblast line, C3H10T1/2, to form aggregates in vitro similar to those found in condensing mesenchyme in vivo (7). In addition, Pln maintained the chondrogenic phenotype of adult chonodrocytes in vitro (7).

Consistent with a fundamental role for Pln in endochondral bone formation, targeted disruption of the Pln gene in mice results in severe disorganization of the columnar structure of chondrocytes and defective endochondral ossification (9). Interestingly, the phenotype of the Pln null mice is similar to that caused by activating mutations of fibroblast growth factor receptor 3 (FGFR3), which has been interpreted to mean that these molecules modulate similar signaling pathways in developing cartilage (9).

Pln is a multi-domain protein consisting of five distinct regions, four of which display sequence similarity to other protein families (10). The proteoglycan and its core protein are disclosed in Costell et al. (16). All the perlecan domains are disclosed in Noonan DM et al. (10).

The N-terminal domain I is unique to Pln. Within domain I are three glycosaminoglycan ("GAG") attachment sites, defined by the consensus amino acid triplet Serine- Glycine- Aspartic Acid ("SGD"). While other potential sites for glycosylation exist in the protein core, the N-terminal sites are considered the major site for GAG attachment (11). Domain II contains repeat sequences highly similar to domain IV of the laminin A chain. In mice, domain III contains an Arginine-Glycine-Aspartic acid ("RGD") sequence but in human Pln this sequence is missing (12). Domain IV contains repeats similar to those found in the IgG superfamily member, neural cell adhesion molecule (N-CAM). The C-terminal of domain V shows sequence similarity to G region of the laminin A. chain. There are also epidermal growth factor (EGF)-like sequences spaced between the domain G-like repeats in Pln domain V.

Each domain of Pln previously has been produced as a recombinant protein, and several of these also have been produced in various forms (13-17).

Perlecan has been associated with growth factors. Mongiat et al. reported that perlecan acts as a ligand reservoir for various growth factors, stabilizing them against misfolding and proteolysis (20). Costell et al. reported that perlecan binds and delivers growth factors in two ways (8). Costell et al. reported that perlecan's heparin sulfate and chondroitin sulfate side chains bind growth factors as well as its protein core.

Several groups have studied the interaction between the glycosaminoglycan molecules and the fibroblast growth factor family of heparin-binding growth factors. For example, Walz et al. have found that the biological activities of fibroblast growth factor-1 and fibroblast growth factor-2 depend on their ability to bind cell surfaces and extracellular matrix heparin sulfate side chains, like those found attached to perlecan (27).

Growth factors have been used as coatings for scaffolds implanted to treat numerous skeletal and connective-tissue related disorders. It is of great interest to attract and retain growth factors to the site of bone or tissue repair and thereby accelerate healing.

Although it is known that perlecan is involved in growth factor retention, the intact molecule is too large to exploit commercially as a growth factor adhesive. Perlecan is one of the most complex gene products because of its enormous dimensions and number of posttranslational modifications. Its size does not allow for efficient and cost effective commercial production. The present invention avoids this problem and meets the needs of the art by providing a molecule that can be produced in large amounts in mammalian cell lines and is at least as active as the intact perlecan molecule in binding and presenting heparin-binding growth factors and inducing differentiation to or maintenance of chondrocyte phenotype.

SUMMARY OF INVENTION

The invention is directed to new uses of proteoglycans to bind and present growth factors, pharmaceutical compositions of such proteoglycans, and medical devices coated with such proteoglycans. The proteoglycan of the invention is derived from domain I of perlecan.

The patent or application file contains at least one drawing executed in color. Copies of this patent or patent application publication with color drawings will be provided by the Office upon request and payment of the necessary fee.

BRIEF DESCRIPTION OF THE DRAWINGS

FIG. 1 depicts the perlecan domains and variants thereof.

FIGS. 2A-D are photographs of the response of C3H10T1/2 cells to recombinant domains of perlecan.

FIGS. 3A-C are photographs of cell cultures from Pln IA coated wells probed with three different antibodies.

FIGS. 4A-B are photographs of C3H10T1/2 cells cultured on Pln IA and Pln I$_{mut}$.

FIGS. 5A-L are photographs of cell aggregation on fragments of perlecan that have been digested with various enzymes.

DETAILED DESCRIPTION

Proteoglycans Useful in the Invention

Preferred embodiments of the invention involve a proteoglycan of less than 450 kDa, more preferably of less than 100 kDa, still more preferably of less than 2 kDa, still more preferably of about 8 to 10 kDa in molecular weight, comprising the core protein of domain I of a mammalian perlecan to which at least one glycosaminoglycan chain is attached. More preferably, the proteoglycan is substituted with two or three glycosaminoglycan chains. The proteoglycans identified as Pln IA and PlnIB, as defined in the attached Example 1, may be used. The proteoglycan should have at least one and can have more glycosaminoglycan chains, varying in length or composition. The invention also includes uses and compositions of proteoglycans in which the core protein comprises an amino acid sequence having at least about 70-75%, still more preferably at least about 80-85%, and most preferably at least about 90% or more homology to the amino acid sequence of domain I of a mammalian perlecan, preferably murine or human perlecan.

Other preferred embodiments of the invention involve a proteoglycan in which the core protein comprises an amino acid sequence of NO:2 and is less than 250 amino acids in length and preferably of less than 200 amino acids in length. The invention also includes uses and compositions of proteoglycans in which the core protein comprises an amino acid sequence having at least about 70-75%, still more preferably at least about 80-85%, and most preferably at least about 90% or more homology to the amino acid sequence of SEQ ID NO:1 or SEQ ID NO:2. Again, as stated before, the proteoglycan should have at least one and can have more glycosaminoglycan chains, varying in length or composition.

To determine the percent homology of two amino acid sequences, the sequences are aligned for optimal comparison purposes (e.g., gaps can be introduced in the sequence of one polypeptide for optimal alignment with the other polypeptide). The amino acid residues at corresponding amino acid positions are then compared. When a position in one sequence is occupied by the same amino acid residue as the corresponding position in the other sequence, then the molecules are homologous at that position (i.e., as used herein amino acid "homology" is equivalent to amino acid "identity"). The percent homology between the two sequences is a function of the number of identical positions shared by the sequences (i.e., % homology=# of identical positions/total # of positions times. 100).

The proteoglycans used in the invention include those molecules having conservative amino acid substitutions at one or more predicted non-essential amino acid residues when compared to a wild-type mammalian perlecan domain I. A "conservative amino acid substitution" is one in which the amino acid residue is replaced with an amino acid residue having a similar side chain. Families of amino acid residues having similar side chains have been defined in the art. These fami-

```
ValThrHisGlyLeuArgAlaTyrAspGlyLeuSerLeuProGluAspIleGluThrVal    (SEQ ID NO: 1)

ThrAlaSerGlnMetArgTrpThrHisSerTyrLeuSerAspAspGluTyrMetLeuAla

AspSerIleSerGlyAspAspLeuGlySerGlyAspLeuGlySerGlyAspPheGlnMet

ValTyrPheArgAlaLeuValAsnPheThrArgSerIleGluTyrSerProGlnLeuGlu

AspAlaGlySerArgGluPheArgGluValSerGluAlaValValAspThrLeuGluSer

GluTyrLeuLysIleProGlyAspGlnValValSerValValPheIleLysGluLeuAsp

GlyTrpValPheValGluLeuAspValGlySerGluGlyAsnAlaAspGlyAlaGlnIle

GlnGlumetLeuLeuArgValIleSerSerGlySerValAlaSerTyrValThrSerPro

GlnGlyPheGlnPheArgArgLeuGlyThrValPro(human) or

ValThrHisGlyLeuArgAlaTyrAspGlyLeuSerLeuProGluAspThrGluThrVal    (SEQ ID NO: 2)

ThrAlaSerArgTyrGlyTrpThrTyrSerTyrLeuSerAspAspGluAspLeuLeuAla

AspAspAlaSerGlyAspGlyLeuGlySerGlyAspValGlySerGlyAspPheGlnMet

ValTyrPheArgAlaLeuValAsnPheThrArgSerIleGluTyrSerProGlnLeuGlu

AspAlaSerAlaLysGluPheArgGluValSerGluAlaValValGluLysLeuGluPro

GluTyrArgLysIleProGlyAspGluIleValSerValValPheIleLysGluLeuAsp

GlyTrpValPheValGluLeuAspValGlySerGluGIyAsnAlaAspGlySerGInIle

GlnGluValLeuHisThrValValSerSerGlySerIleGlyProTyrValThrSerPro

TrpGlyPheLysPheArgArgLeuGlyThrValProGln (mouse).
```

Further preferred embodiments involve a proteoglycan comprising the amino acid sequence of SEQ ID NO: 1 or SEQ ID lies include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in the proteoglycan is preferably replaced with another amino acid residue from the same side chain family such that the proteoglycan retains the ability to bind growth factors. More preferably, the proteoglycans retain the ability to facilitate the formation of aggregates of C3H10T1/2 cells.

In other preferred embodiments, the proteoglycan is a biologically active portion of the perlecan domain I that includes a domain or motif that has growth factor binding ability and/or the ability to support C3H10T1/2 cell agglomeration. Such domains or motifs include the domains associated with glycosaminoglycan attachment to the core polypeptide.

The proteoglycans of the invention may be synthesized in various ways, such as by chemical synthesis, isolation from perlecan, or recombinant production. Preferred is recombinant production. Examples of such production are found in Costell et al. (16). Costell et al. teaches preparation of perlecan domain I from mammalian cell clones on a preparative scale using the pRc/CMV expression vector sold by Invitrogen. The expression vector was cotransfected together with plasmid $pSV_{pac}$ into human embryonic kidney 293 cells and stable transfectants were selected with puromycin.

The proteoglycans used in the invention may be obtained by derivation from perlecan from any mammalian species, most preferably mouse, rat, or human.

The proteoglycans of the invention may be used to induce differentiation to or maintenance of connective-tissue cells, particularly chondrocytes. More particularly, chondrocyte phenotype can be maintained in cultures using the inventive proteoglycans. The proteoglycans may also be used to bind and present heparin-binding growth factors. The proteoglycans may be used in soluble or insoluble form. They also may be used as a coating for surfaces, particularly surfaces used in tissue engineering or prosthetic devices. For example, scaffolds and medical devices may be coated with the inventive proteoglycans and implanted in a mammalian body. The coating binds growth factors to the surface, which encourages rapid and complete tissue growth at the injured site. Also, the surfaces may be coated with the inventive proteoglycans to which growth factors are attached and then implanted into a mammalian body. These coated scaffolds and devices are expected to provide enhanced recovery for patients suffering from connective tissue disorders, such as bone fractures, cartilage tearing, etc. The inventive proteoglycans increase the adhesion of desirable biological materials such as growth factors to the repair site.

Scaffolds

Devices coated with the proteoglycans of the invention such as implants and scaffolds are also provided. Also provided are implants and scaffolds coated with the proteoglycans of the invention to which growth factors have been attached, either covalently or non-covalently.

Preferably, the scaffold is made of a polymer, a biologically derived material, ceramic, metal, or combinations thereof, that is biologically inert and physiologically compatible with mammalian tissues. The scaffold material preferably does not induce an inflammatory response. The scaffold also preferably is capable of associating with the proteoglycan at sufficient levels to satisfy the intended objective, e.g., increased growth factor adhesion or attraction to the scaffold. The scaffold can bind the proteoglycan either covalently or non-covalently, such as by electrostatic charge or hydrophobic or hydrophilic interactions.

Preferred polymers are polyamides, polypeptides, polyesters, polycarbonates, polyurethanes, polyacetals, polysaccharides, and polyolefins. Specific examples of such polymers include silicone rubber, polyurethane rubber, polyethylene, polyvinyl chloride, poly (hydroxyethyl methacrylate), poly (methyl methacrylate), poly (ethyleneterephthalate), polypropylene, polystyrene, poly (tetrafluoroethylene), polyglycolic acid, cellulose, ethylcellulose, methylcellulose, dextran, carboxymethylcellulose, hyaluronic acid, hydroxypropylmethylcellulose, nylon, collagen, and collagen-GAG. Preferred polymers include expanded polytetrafluoroethylene composed of two polymers and having nine billion pores per square inch. Additionally, the scaffold can be a copolymer, composite or blend of the above polymers.

The polymer may have other materials embedded in it, such as carbon fibers embedded in a polyurethane-poly(L-lactide matrix). Additional scaffold materials are disclosed in Sweigart, M. A. (28). Additional scaffold materials are known to those skilled in the art.

Preferred biologically derived materials are matrices comprised of collagen sponge, cortical bone chips, cancellous bone chips, cortico-cancellose bone chips, hydroxyapatite or like ceramics, bioactive glass, growth factors and demineralized bone, which are imbedded or suspended in a carrier material. The carrier material is preferably a fibrin-containing composition that coagulates, collagen formulations, hydroxylapatite, pleuronic polymers, synthetic or natural polymers, carboxymethylcellulose, gelatin, or combinations thereof. More preferably, the carrier is gelatin derived from human or animal tissue. Other preferred biologically derived materials are mammalian tissues, such as perichondral tissue and periosteal tissue.

Methods of Treatment

The proteoglycans of the invention can also be administered directly to injured connective tissue, where growth factors will be attached in vivo and thereby tissue recovery will be enhanced. Growth factors can also be attached to the proteoglycans ex vivo and then the proteoglycan/growth factor product can be administered to a damaged tissue, such as a bone fracture or cartilage tear. The proteoglycan may be in soluble or insoluble form.

The invention provides a method for accelerating wound, tissue, or bone healing in a mammalian subject, e.g., human, by applying to the injured area a therapeutically effective amount of a composition which contains one or more of the proteoglycans of the invention and optionally a heparin-binding growth factor. In addition, the invention provides for pharmaceutical composition comprising one or more of the proteoglycans of the invention or a biologically active portion thereof, a pharmaceutically acceptable carrier, and optionally a heparin-binding growth factor.

The proteoglycans can be used to administer or attract growth factors as treatment for a variety of medical conditions. One important example is in the repair of bone, cartilage, or other connective tissue (such as tendon and ligament). Repair may be needed because of trauma, bone tumor resection, or in the case of joint fusion and spinal fusion for non-healing fractures and osteoporotic lesions. A proteoglycan-coated scaffold also may be used in treating tooth and jaw defects in cases of trauma, bone loss, tooth loss, and gum disease. The scaffolds also are useful in treating cartilage defects such as those which result from rheumatoid arthritis, osteoarthritis and trauma. The scaffolds also may be used to repair defects and damage in skin, muscle and other soft tissues such as results from trauma, burns, ulcers (diabetic ulcers, pressure sores, venus, stasis ulcers, etc.). Likewise, damage to visceral organs including liver damage, heart attack damage, and damage resulting from intestinal cancer or intestinal ulcer may be treated with the scaffolds of the invention.

The proteoglycans of the invention may be administered with growth factors attached or without growth factors attached, such that growth factors already present in the mammalian body can be attracted to and bind to the proteoglycan.

Various heparin-binding growth factors are known in the art or are readily identifiable and can be used in the invention. For example, U.S. Pat. No. 5,876,730 to Brigstock et al. issued Mar. 2, 1999 entitled "Heparin-binding growth factor (HBGF) polypeptides" discloses a group of heparin-binding growth factors isolated from uterine secretory fluids. Another example is transforming growth factor-.beta. Many members of the fibroblast growth factor family ("FGF family") also bind tightly to heparin.

The invention also pertains to in vitro culture of cells with the purpose of creating tissue constructs for repairing tissues and organs in vivo. The scaffolds may be used to promote tissue culture of committed cells and/or differentiation of precursor cells. Thus, the scaffolds of the invention can be used in virtually all instances when it is desirable to provide a substrate for the growth of cells onto or into a tissue replaceable matrix. Scaffolds can also be used with autografts, allografts, and xenografts associated with bone grafts, cartilage grafts, and joint resurfacing implants.

EXAMPLES

The following discussion shows that in C3H10T1/2 cells, domain I of perlecan functions to trigger the cells to enter a chondrogenic differentiation pathway.

Example 1

Materials and Methods

Materials

Pln/HSPG2 was obtained from Becton-Dickinson Labware (Bedford, Mass.). The rabbit polyclonal antibody against rat aggrecan was provided by Dr. Kurt Doege (Shriner's Hospital for Children, Portland Unit). The rabbit anti-mouse antibody against type X collagen (PXNC1-88) was provided by Dr. Greg Lunstrum (Shriner's Childrens Hospital, Portland, Oreg.) The rabbit IgG antibody against mouse type II collagen was purchased from Biodesign International (catalog # T40025R). Species-specific, Texas-Red conjugated secondary antibodies were purchased from Amersham Corporation (Arlington Heights, Ill.).

Immunofluorescent Detection of Extracellular Matrix Components

After culture upon matrix for 6 or 9 days, cell aggregates and monolayers were rinsed twice with Dulbecco's phosphate buffered saline (D-PBS) without calcium or magnesium. The specimens were subsequently fixed, washed 3 times (5 minutes at room temperature) with D-PBS and incubated with the primary antibody for 1 hr at 37° C. in a humidified chamber. After 3 washes (5 min each at room temperature) in D-PBS, cell aggregates and monolayers were incubated with the secondary antibody for 45 min at 37° C. in a humidified chamber, and finally washed 3 times (5 min each) with D-PBS and mounted.

For aggrecan labeling, cell aggregates and monolayers were fixed in 100% methanol (10 min/at rpp, temperature); however, for type II and X collagen labeling an ice cold solution composed of 95% ethanol plus 5% acetic acid (30 min on ice) was employed as fixative. To promote type II and X collagen antibody penetration, cell aggregates and monolayers were incubated with 0.02% Type 1V-S testicular hyaluronidase (H3884, Sigma) for 30 min at room temperature.

Culture of C3H1OT1/2 Cells on Various Matrix Components

Cell culture was performed as previously described (7) with some modification. For confocal microscopic analysis of cell aggregates, Nalge-Nunc "pennanox" chambered slides (4 well, catalogue # 177437) were used in place of the Nalge-Nunc four well plates used previously. Briefly, for coating wells, 5 µg of Pln or recombinant protein plus D-PBS was added to the well at a final volume of 200 µl, and then incubated overnight at 37° C. with lids askew. On the following day, wells were rinsed twice with D-PBS prior to addition of cells. C3H1OT1/2 cells were added to wells at a density of $2 \times 10^5$ cells per well in CMRL-1066 matrix. The CMRL1066 media (Gibco Life Sciences, Rockville, Md.) was supplemented with 15% (v/v) fetal calf serum, 100 U/ml penicillin and 100 mg/ml streptomycin sulfate, ascorbic acid (50 µg/ml), citrate (50 µg/ml), and pyruvate (50 µg/ml), and changed daily throughout the experiment. Great care was taken not to disturb or remove aggregates. Formation of aggregates was assessed by visual inspection using light microscopy. Cells that had drawn together into dense, multi-layered cellular aggregates reminiscent of condensing mesenchyme of developing cartilage, leaving areas of the well bare, were scored as positive as described previously (7).

Confocal Microscopic Analysis of C3HJ OTJ/2 Cell Aggregates

All data was acquired on a Zeiss inverted 1OO M Axioskop equipped with a Zeiss 510 LSM confocal microscope and a Krypton Argon laser (48 8 nm and 568 nm excitation lines). Simultaneous acquisition of nuclei stained with Syto 13(505-550 band pass filter) and Texas Red-conjugated secondary antibodies (590 long pass filter) utilized the fast-line switch feature for elimination of spectral bleedthrough. Samples were imaged using a Zeiss 63X C-Apochromat water immersion lens (N.A. 1.2).

Enzymatic Digestion of Glycosaminoglycan Chains

Digestion with both heparinase and chondroitinase ABC was performed as described previously (7). Briefly, wells coated with Pln or recombinant domains of Pln were subjected to digestion with chondroitinase ABC or a mixture of heparinases I, II, III (Sigma, St. Louis, Mo.) for 4 hrs at 37° C. After digestion, the enzyme solution was removed and wells were rinsed once with DPBS before the cells were plated.

Recombinant Pln Fragments

Recombinant Pln fragments were prepared as described previously (13-17). Briefly, cDNA encoding the specified Pln domain was inserted in frame behind the basement membrane protein, BM-40. This construct was then inserted into the pRc/CMV vector and stably transfected into human embryonic kidney 293 cells. Positive clones were selected and media containing the various domains collected. Recombinant protein was isolated by elution from a DEAE-cellulose column using a NaCl gradient and purity assessed by SDS-PAGE and Coomassie Blue Staining.

Results

Figure 1:
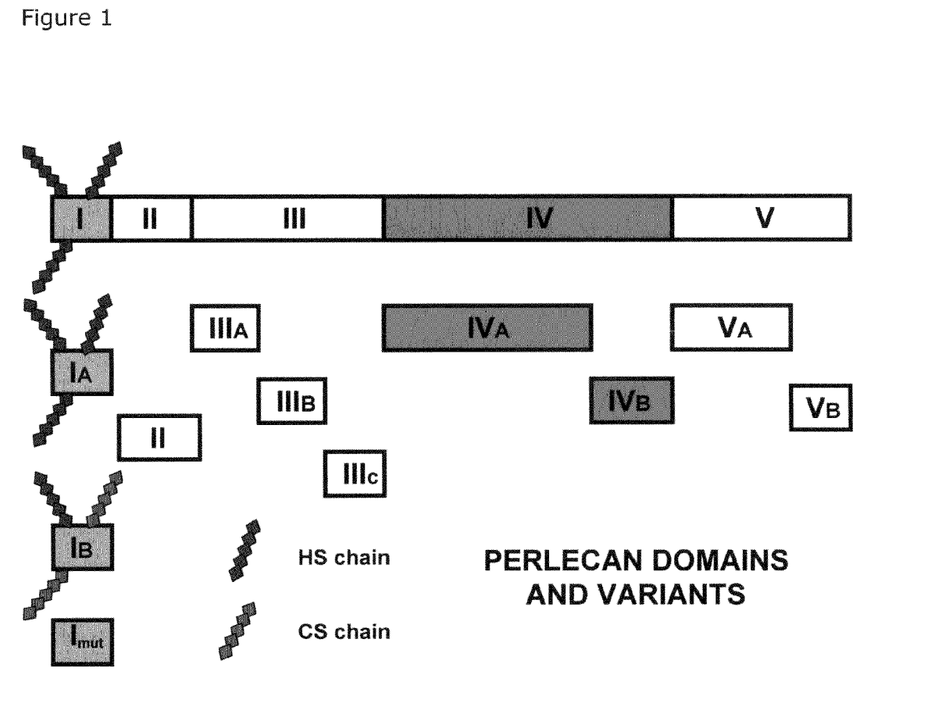
Figure 2:
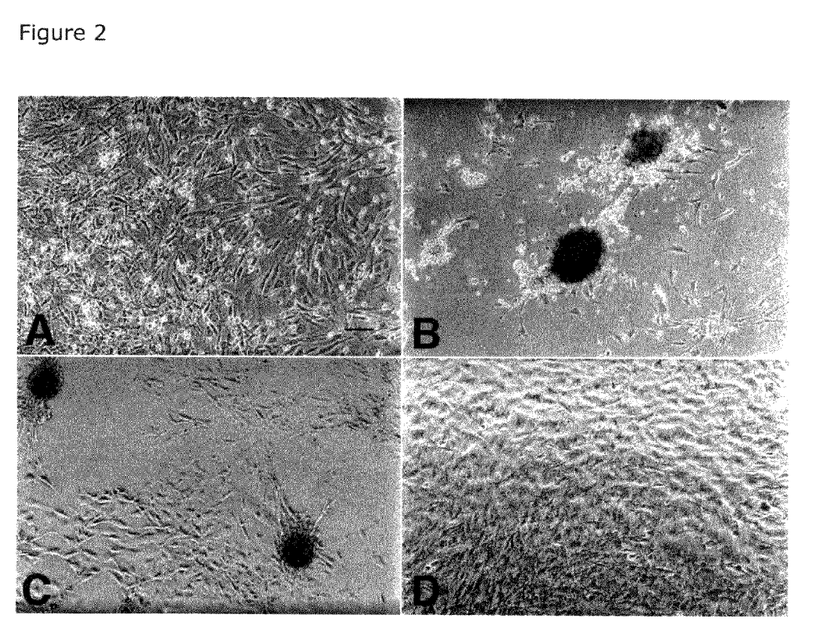
Figure 3:
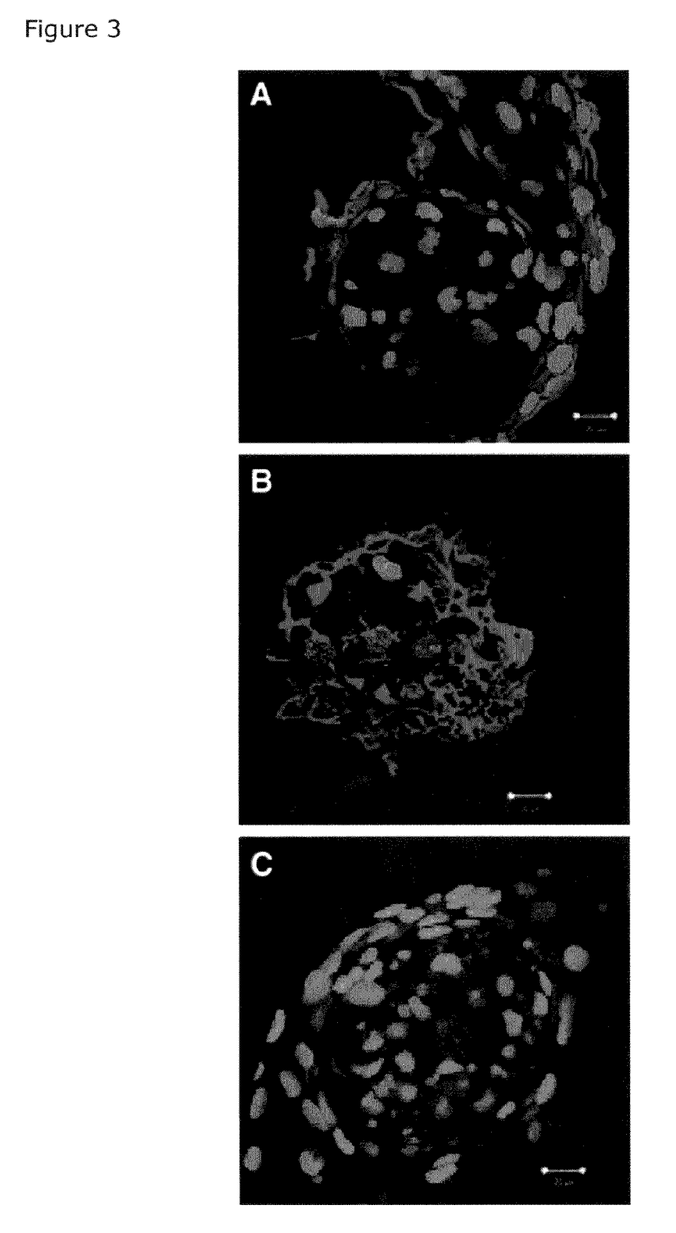

The Response of C3H1OTI/2 Cells Cultured on Domain I of Pln Mimics the Response Generated by Native Pln It was reported previously that the murine embryonic cell line, C3H1OT1/2, aggregates and undergoes chondrogenic differentiation in response to culture on Pln coated surfaces (7). The present investigation tested the hypothesis that a single domain of the Pln molecule is responsible for the in vitro aggregation and chondrogenic activation of C3H10T1/2 cells. To test this hypothesis, recombinant fragments (table I) of Pln were used as culture matrices for C3H10T1/2 cells (FIG. 1). When cultured on the recombinant N-terminal domain, Pln IA, C3H10T1/2 cells responded as if cultured on native Pln (FIG. 2, compare B and C). Within 24 hrs, the majority of the cells condensed into multi-cellular masses of rounded cells, leaving the well bare with relatively few fibroblastic cells between the aggregates. By day 6 of culture, aggregates express markers of early chondrogenesis (Alcian Blue (not shown), type II collagen, and aggrecan, FIG. 3), but not type X collagen, a marker of chondrocyte maturation. Analysis of day 6 aggregates employing confocal microscopy indicates the cells are tightly packed and in high density. Z-series (optical sectioning) analysis of aggregates labeled with the nucleic acid stain Syto 13 (Molecular Probes, catalogue #S-7575) revealed that aggregates vary in thickness (42-12O μm). In addition, z-series analysis of aggregates labeled with antibodies specific to type II collagen and aggrecan illustrated that expression of these chondrogenic markers is localized to the periphery of the aggregate. Interestingly, expression of type II collagen appears to encompass the entire aggregate surface; however, aggrecan expression is distributed only at the top/dorsal surface of the aggregate (FIG. 3, A and B).

In contrast to Pln IA, C3H10T1/2 cells did not aggregate or differentiate when cultured on other recombinant Pln domains, Pln II through Pln V(B) (FIG. 2D). C3H10T1/2 cells cultured on recombinant Pln domains II-V(B) responded like cells cultured on plastic, they attached, spread, and formed a dense monolayer. Thus, domain I of Pln is sufficient for the aggregation and differentiation of C3H10T1/2 cells into early chondrocytes in vitro.

The Presence of GAG Chains is Required on the Pln IA Core for Activity

Heparinase digestion of native Pln has been shown to greatly reduced its aggregate-inducing activity in vitro (7). Thus, in the present investigation we tested the hypothesis that the presence of GAG chains on recombinant Pln domain I is necessary for the aggregation and differentiation of C3H10T1/2 cells in vitro. To test this hypothesis, recombinant Pln domain I variants of differing GAG chain composition were employed as culture matrices for C3H10T1/2 cells. Of the three Pln domain I variants, the first comprised a protein core bearing HS chains only (Pln IA), the second bearing a mixture of HS and CS chains (Pln 1B; (16)), and the third with mutations preventing GAG chain attachment (Pln $I_{mut}$).

Figure 4:
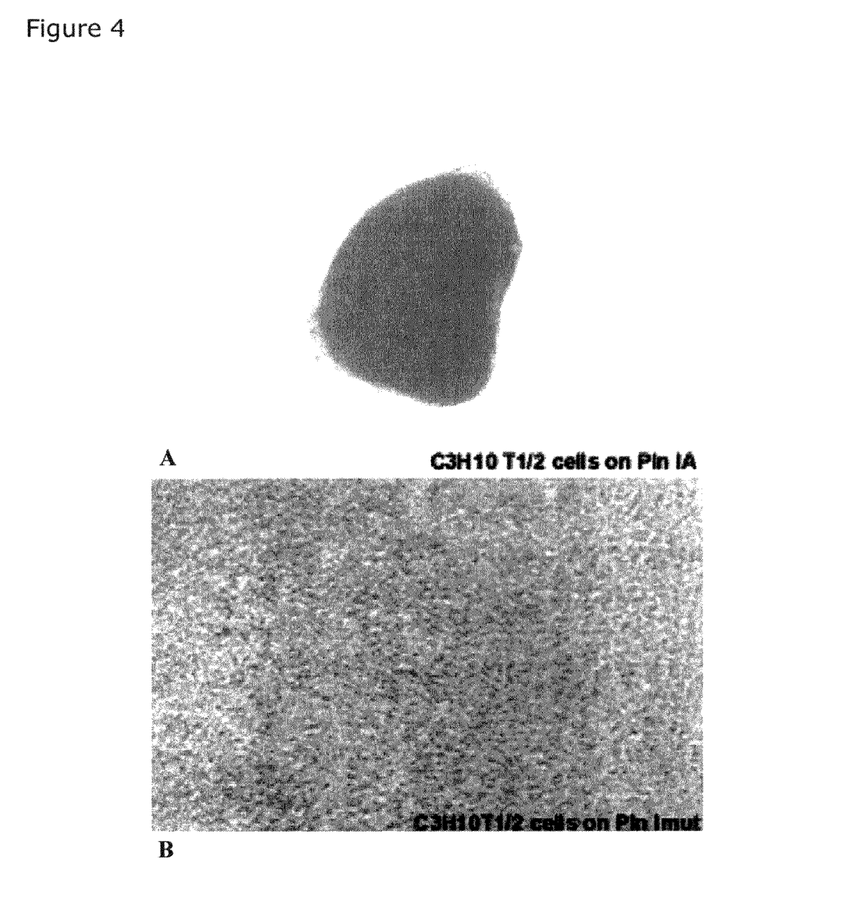

When cultured on Pln IA and IB, a robust recruitment of C3H10T1/2 cells into aggregates was observed (FIG. 4). This response is consistent with previous observations of cells cultured on native Pln (7). In contrast, C3H10T1/2 cells cultured on Pln $1_{mut}$ not aggregate but attach and spread into a dense monolayer (FIG. 4). The full activity observed with Pln IB suggests that the presence of CS in conjunction with HS chains on the protein core does not interfere with activity. Moreover, our observations employing Pln $I_{mut}$ suggest that the presence of GAG chains on the Pln protein core is necessary for C3H10T1/2 cell aggregation and differentiation activity.

Figure 5:
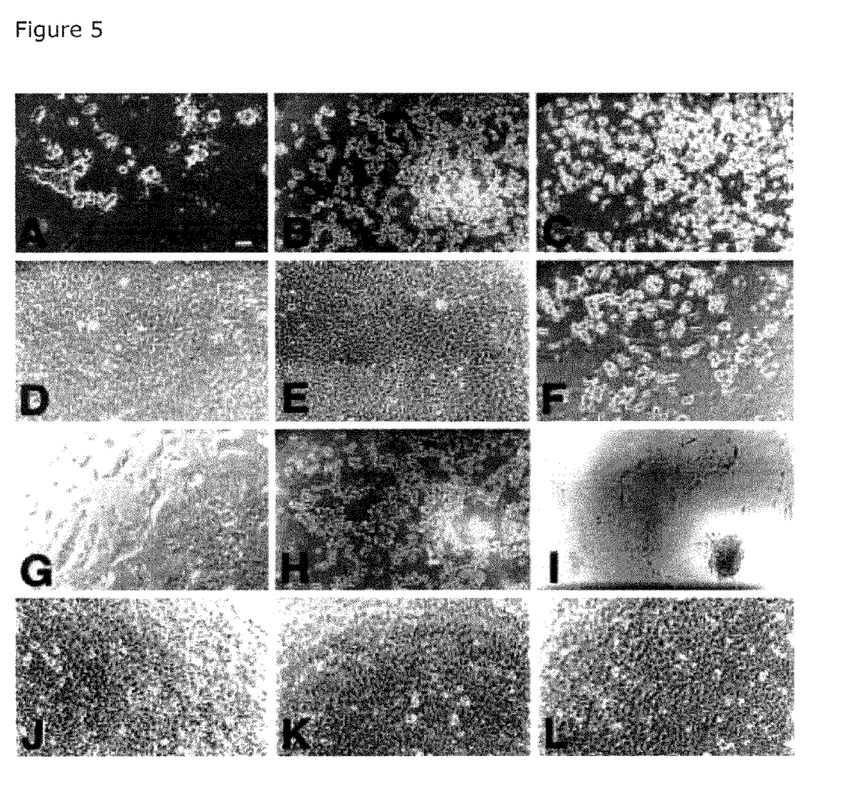

Enzymatic Digestion of GAG Chains Reveals Chondroitin/Dermatan Sulfate Chain Participation The redundancy in function between the Pln IA and Pln 1B forms of Pln domain I suggested that both HS and chondroitin/dermatan sulfate chains might play a role in supporting differentiation. If a soluble factor secreted by the cells acted by binding HS, then digestion with heparinase should result in a reduction or loss of this activity. Thus, both Pln IA and Pln IB variants were digested with either heparinase or chondroitinase ABC and tested in the aggregation assay. As expected, heparinase, but not chondroitinase digestion abolished the aggregate-promoting activity of native Pln (FIG. 5, panels A, D, G, and J). Similarly, activity of the HS-bearing Pln IA variant was only lost when digested with heparinase, but not with chondroitinase ABC (FIG. 5, panels B, E, H, and K). Interestingly, neither digestion with heparinase nor chondroitinase ABC alone affected the activity of the Pln IB variant (FIG. 5, panels C, F and I). The maintenance of activity after heparinase digestion suggested that chondroitin/dermatan sulfate chains carried by the Pln IB variant also could promote aggregate formation. This was confirmed by the demonstration that digestion with a combination of enzymes destroyed aggregate promoting activity (FIG. 5L). Thus, either HS or chondroitin/dermatan sulfate chains on Pln domain I is sufficient to trigger this response.

Discussion

After culturing the cells on each perlecan domain individually, it was found that the N-terminal GAG-bearing domain I of Pln was sufficient to activate aggregate formation and expression of chondrogenic markers. No other domain had this aggregating ability, and C3H10T1/2 rapidly attached and spread on other recombinant domains. From this we conclude that Pln I with its attached GAG chains, like intact Pln, provides a sufficient signal to initiate the chondrogenic program in C3H10T1/2 cells.

The contribution of the core protein and GAG chains to the activity of domain I was explored further using Pln domain I variants of differing GAG composition or mutated to delete sites of GAG chain addition. We also tested the activity of preparations that had been digested with GAG lyases. The finding that Pln $I_{mut}$ displayed no aggregate-forming activity indicated a requirement for the presence of GAG chains and showed that the Pln I core protein alone provided an insufficient signal. This idea was further supported by the finding that heparinase digestion of Pln IA completely destroyed its activity. Because neither heparinase nor chondroitinase ABC digestion alone could destroy the aggregate-promoting activity of Pln IB having mixed GAG chains, we conclude that either heparin sulfate or chondroitin sulfate GAG chains attached to domain I can support aggregation and chondrocytic differentiation of C3H10T1/2 cells.

Interestingly, the pattern of expression of chondrogenic markers within aggregates forming in vitro suggests that the aggregate itself is not homogenous. For example, whereas collagen II is expressed uniformly at the periphery of the aggregates, aggrecan appears to be expressed primarily at the top of the aggregate where the most differentiated cells are expected to be. The pattern of aggregate expression resembles that previously reported for N-CAM (23) where it was suggested that within aggregates a "sorting out" between differentiating and non-differentiating cells occurs. This marker localization is seen in aggregates on Pln domain I, providing further evidence that this region produces a sufficient signal for early chondrogenesis.

FIG. 1. Recombinant Fragments of Pln Protein

The Pln core protein was expressed as a series of recombinant polypeptides in human 293 embryonic kidney cells and isolated by ion exchange chromatography as described in the text. Domains I (Pin IA) and II (Pln II) were both expressed as intact domains while domains III, IV and V were expressed as smaller proteins. The three subdomains found in domain III were each represented by a recombinant polypeptide, Pln III(A-C) while domain IV was divided into unequal Pln IV(A, B). Domain V also contained subdomains, expressed as recombinant fragments Pln V(A, B) Two variant forms of domain I were expressed. Pln IB with a protein sequence identical to Pln IA, carried both HS and chondroitin/dermatan sulfate chains on its protein core. The nucleotide sequence of Pln $I_{mut}$ was altered such that the amino acid motifs used to attach glycosaminoglycan chains were no longer present. Thus, this form of domain I carries no glycosaminoglycan chains.

FIG. 2. Response of C3H10T1/2 Cells to Recombinant Domains of Pln

C3H10T1/2 cells were either cultured on plastic (A), native Pln (B), Pln IA (C), or on domains II-V (D). On plastic (A), cells appeared fibroblastic while on native Pln (B) and Pln IA alone (C) cells formed aggregates. However, when domains II thru V were used individually as matrices on which C3H10T1/2 cells were cultured, no aggregates formed. Panel D presents a representative view of C3H10T1/2 cells when cultured on any of the Pln domains II thru V. The cells form a dense monolayer of fibroblastic cells.

FIG. 3. Pln Domain IA Induces Differentiation to the Same Extent as Native Pln

Cultures (day 6) from Pln IA coated wells were probed with antibodies to type II collagen (A, red signal), aggrecan (B, red signal), type X collagen (C, red signal), and optically sectioned with a confocal microscope (0.2 μm). The green signal is the nucleic acid stain Syto 13. Type II collagen is expressed on the exterior surface of Pln IA aggregates. In contrast, aggrecan expression is localized at the top/dorsal surface of the Pln IA aggregate. Day 6 Pln IA aggregates do not express type X collagen. Magnification bar equals 20 μm.

FIG. 4. Induction of Morphological Change by Pln IA Variants

C3H10T1/2 cells were cultured on Pln IA and Pln $I_{mut}$ (lacking glycosaminoglycan chains) and photographed on day 6 of culture. C3H10T1/2 cells cultured on Pln $I_{mut}$ did not form aggregates.

FIG. 5 Activity of Enzymatically Modified PG IA and PG IB

Enzymatic digestion of Pln IA and Pln IB was performed to examine the role of glycosaminoglycan chains in differentiation of C3H10T1/2 cells. Cells on undigested native Pln (A), Pln IA (B) or Pln IB (C) formed numerous aggregates. When digested with heparinase, Pln (D)) and Pln IA (E) failed to stimulate the C3H10T1/2 cells while cells cultured on Pln IB (F) again formed aggregates. Chondroitinase ABC digestion had little effect on Pln (G), Pln IA (H) or Pln IB (I). The combination of the two enzymes resulted in loss of activity in all cases; Pln (J), Pln IA (K), Pln IB (L). Magnification bar in panel B-100 μM.

TABLE I

| Aggregate formation on Pln domains[1] | |
|---|---|
| Matrix Component | Response |
| PBS | (−) |
| Pln | (+++) |
| Pln IA | (++/+++) |
| Pln IB | (+++) |

TABLE I-continued

| Aggregate formation on Pln domains[1] | |
|---|---|
| Matrix Component | Response |
| Pln $I_{mut}$ | (−) |
| Pln II | (+/−) |

[1]C3H10T1/2 cells were cultured on the indicated Pln domain and aggregation and Alcian Blue staining assessed after 3 days as described previously (7). (−), no aggregates or Alcian Blue staining; (+/−), inefficient aggregate formation with little or no Alcian Blue staining; (++), efficient aggregate formation with heterogeneous Alcian Blue staining; (+++), efficient aggregate formation and homogeneous Alcian Blue staining.

Pln III (A-C) (−)
Pln IV (A-C) (−)
Pln V (A,B) (−)

References

The following references are hereby incorporated in their entireties herein:

1. Reddi A H 1995 Cartilage morphogenesis: role of bone and cartilage morphogenetic proteins, homeobox genes and extracellular matrix. Matrix Biol 14(8):599-606.
2. Lanske B, Ainling M, Neff L, Guiducci J, Baron R, Kronenberg H M 1999 Ablation of the PTHrP gene or the PTH/PTHrP receptor gene leads to distinct abnormalities in bone development. J Clin Invest 104(4):399-407.
3. Iwamoto M, Enomoto-lwatnoto M, Kurisu K 1999 Actions of hedgehog proteins on skeletal cells. Crit Rev Oral Biol Med 10(4):477-86.
4. Matsunaga S, Yamamoto T, Fukumura K 1999 Temporal and spatial expressions of transforming growth factor-betas and their receptors in epiphyseal growth plate. Int J Oncol 14(6):1063-7.
5. Chintala S K, Miller R R, McDevitt C A 1994 Basic fibroblast growth factor binds to heparan sulfate in the extracellular matrix of rat growth plate chondrocytes. Arch Biochem Biophys 310(1):180-6.
6. Ornitz D A 2000 FGFs, heparan sulfate and FGFRs: complex interactions essential for development. BioEssays 22:108-112.
7. French M M, Smith S E, Akanbi K, Sanford T, Hecht J, Farach-Carson M C, Carson D D 1999 Expression of the heparan sulfate proteoglycan, perlecan, during mouse embryogenesis and perlecan chondrogenic activity in vitro. J Cell Biol 145(5):1 103-15.
8. Costell M, Gustafsson E, Aszódi A, Mörgelin M, Bloch W, Hunziker E, Addicks K, Timpl R, Fässler R 1999 Perlecan maintains the integrity of cartilage and some basement membranes. J Cell Biol 147:1109-1122.
9. Arikawa-Hirasawa E, Watanabe H, Takami H, Hassell J R, Yamada Y 1999 Perlecan is essential for cartilage and cephalic development. Nat Genet 23(3):354-8.
10. Noonan D M, Fulle A, Valente P., Cal S., Horigan E, Sasaki M, Yamada Y, Haskell J R 1991. The complete sequence of perlecan, a basement membrane heparin sulfate proteoglycan, reveals extensive similarity with laminin A chain, low density lipoprotein-receptor, and the neural cell adhesion molecule. J Biol Chem 266(34):22939-47.
11. Murdoch A D, Dodge G O, Cohen I, Tuan R S, Iozzo R V 1992 Primary structure of the human heparan sulfate proteoglycan from basement membrane (HSPG2/perlecan). A chimeric molecule with multiple domains homologous to 12. Cohen I R, Grassel 5, Murdoch A D, Iozzo R V 1993 Structural characterization of the complete human perlecan gene and its promoter. Proc Natl Acad Sci 90(21): 10404-8.
13. Costell M, Sasaki T, Mann K, Yamada Y, Timpl R 1996 Structural characterization of recombinant domain II of the basement membrane proteoglyean perlecan. FEBS Lett 396(2-3):127-3 1.
14. Schulze B, Sasaki T, Costell M, Mann K, Timpl R 1996 Structural and cell-adhesive properties of three recombinant fragments derived from perlecan domain III. Matrix Biol 15(5):349-57.
15. Brown J C, Sasaki T, Gohring W, Yamada Y, Timpl R 1997 The C-terminal domain V of perlecan promotes betal integrin-medicated cell adhesion, binds heparin, nidogen and fibulin-2 and can be modified by glycosaminoglycans. Eur J Biochem 250(1):39-46.
16. Costell M, Mann K, Yamada Y, Timpl R 1997 Characterization of recombinant perlecan domain I and its substitution by glycosaminoglycans and oligosaccharides. 243(1-2):1 15-21, Eur. J. Biochem.
17. Sasaki T, Fukai N, Mann K, Gobring W, Olsen B R, Timpl R 1998 Structure, function and tissue forms of the C-terminal globular domain of collagen XVIII containing the angiogenesis inhibitor endostatin. EMBO J 17(15):4249-56.
18. Timpl R 1993 Proteoglycans of basement membranes. Experientia 49(5):417-28.
19. SundarRaj N, Fite D, Ledbetter S. Chakravarti 5, Hassell J R 1995 Perlecan is a component of cartilage matrix and promotes chondrocyte attachment. J Cell Sd 108(Pt 7):2663-72.
20. Mongiat M, Taylor K, Otto J, Abc 5, Uitto J, Whitelock J M, Iosso R V 2000 The protein core of the proteoglycan perlecan binds specifically to fibroblast growth factor-7. J Biol Chem 275(10):7095-7 100.
21. Whitelock J M, Graham L D, Melrose 1, Murdoch A D, Iozzo R V, Underwood Pa. 1999 Human perlecan immunopurified from different endothelial cell sources has different adhesive properties for vascular cells. Matrix Bio 19(2):163-78.
22. San Antonio I D, Winston B M, Tuan R S 1987 Regulation of chondrogenesis by heparan sulfate and structurally related glycosaminoglycans. Dev Biol 123:17-24.
23. Tavella S, Raffo P. Tacchetti C, Cancedda R, Castagnola P 1994 N-CAM and N-Cadherin expression during in vitro chondrogenesis. Experimental Cell Research 215:354-362.
24. Perrinion N, Bernfield M 2000 Specificities of heparan sulphate proteoglycans in developmental processes. Nature 404(6779):725-8
25. Mello M A, Tuan R S 1999 High density micromass cultures of embryonic limb bud mesencbymal cells: an in vitro model of endochondral skeletal development. In vitro Cell Dev Biol Anim 35(5):262-9.
26. Solursh M 1991 Formation of cartilage tissue in vitro. I Cell Biochem 45(3):258-60.
27. Walz A 1997 Essential role of heparin sulfates in axon navigation and targeting in the developing visual system. Devel. 124:2421-2430.
28. Sweigart M A (2001) Tissue Engineering 7:2: 111-128.

What is claimed is:

1. A method for accelerating cartilage repair at a repair site in a mammal comprising applying at the repair site a therapeutically effective amount of a proteoglycan that comprises the amino acid sequence of the core protein of domain I of a mammalian perlecan to which at least one heparan sulfate glycosaminoglycan is attached, wherein the proteoglycan consists of 200 or fewer amino acids and stimulates mesenchymal stem cell differentiation to cartilage.

2. The method of claim 1 wherein at least one heparin-binding growth factor is attached to the proteoglycan.

3. The method of claim 1 wherein the proteoglycan consists of domain I of perlecan.

4. The method of claim 1 wherein the mammalian perlecan is mouse, rat, or human perlecan.

5. The method of claim 1, wherein the proteoglycan is coated on an implantable scaffold.

6. A method for accelerating cartilage repair at a repair site in a mammal comprising applying at the repair site a therapeutically effective amount of a proteoglycan that consists of an amino acid sequence having at least 84% homology to SEQ ID NO:1, to which at least one heparan sulfate glycosaminoglycan is attached, wherein the proteoglycan consists of 200 or fewer amino acids and stimulates mesenchymal stem cell differentiation to cartilage.

7. The method of claim 1 wherein the mammal is suffering from cartilage defects resulting from rheumatoid arthritis, osteoarthritis or trauma.

8. The method of claim 6 wherein the mammal is suffering from cartilage defects resulting from rheumatoid arthritis, osteoarthritis or trauma.

9. The method of claim 1, wherein the proteoglycan consists of the amino acid sequence of the core protein of domain I of a mammalian perlecan to which at least one heparan sulfate glycosaminoglycan is attached.

10. The method of claim 9, wherein the amino acid sequence of the core protein of the proteoglycan is SEQ ID NO:1 or SEQ ID NO:2.

* * * * *